(12) United States Patent
Illes et al.

(10) Patent No.: US 6,656,921 B1
(45) Date of Patent: Dec. 2, 2003

(54) USE OF ZINC HYALURONATE AGAINST PEPTIC ULCER

(75) Inventors: Janos Illes, Budapest (HU); Judit Matuz, Budapest (HU); Erzsabet Neszmelyi, Budapest (HU); Gaborne Forrai, Budapest (HU); Bela Stefko, Budapest (HU); Katalin Saghy, Budapest (HU); Laszlo Szporny, deceased, late of Budapest (HU), by Gyula Szporny legal representative.

(73) Assignee: Richter Gedeon Vegyeszeti Gyar RT., Budapest (HU)

( * ) Notice: Subject to any disclaimer, the term of this patent is extended or adjusted under 35 U.S.C. 154(b) by 0 days.

(21) Appl. No.: 09/403,714

(22) PCT Filed: Apr. 28, 1998

(86) PCT No.: PCT/HU98/00044

§ 371 (c)(1),
(2), (4) Date: Sep. 21, 2000

(87) PCT Pub. No.: WO98/48815

PCT Pub. Date: Nov. 5, 1998

(30) Foreign Application Priority Data

Apr. 29, 1997 (HU) .............................. 9700826

(51) Int. Cl.⁷ ............................................. A61K 31/715
(52) U.S. Cl. ......................................................... 514/54
(58) Field of Search ........................................... 514/54

(56) References Cited

U.S. PATENT DOCUMENTS

| | | |
|---|---|---|
| 5,472,950 A | 12/1995 | Burger et al. |
| 5,554,598 A | 9/1996 | Burger et al. |
| 6,458,774 B1 * | 10/2002 | Burger et al. ................. 514/54 |

FOREIGN PATENT DOCUMENTS

| | | |
|---|---|---|
| JP | 6-48950 | 2/1994 |
| WO | 9810773 | * 3/1998 |
| WO | WO 98/48815 | 11/1998 |

* cited by examiner

Primary Examiner—Dwayne C. Jones
Assistant Examiner—C. Delacroix-Muirheid
(74) Attorney, Agent, or Firm—Herbert Dubno; Jonathan Myers (57) ABSTRACT

The invention relates to pharmaceutical compositions against peptic ulcer as well as to a method of treating peptic ulcer. The compositions contain and the method of treatment employs zinc hyaluronate as an active ingredient having a molecular weight in the range of 500,000 to 1,200,000 daltons.

4 Claims, 1 Drawing Sheet

Figure 1

Effect of Zn-hyaluronate (II), Zn-hyaluronate (M) and Sucralfate on acetic acid-induced chronic gastric ulcer

USE OF ZINC HYALURONATE AGAINST PEPTIC ULCER

This application is a 371 of Pct/Hu98/00044 filed Apr. 28, 1998.

FIELD OF THE INVENTION

The invention relates to pharmaceutical compositions with activity against peptic ulcer containing a zinc associate (complex) of hyaluronic acid as well as a process for the preparation thereof.

The invention furthermore relates to the use of the zinc associate (complex) of hyaluronic acid, i.e. zinc hyaluronate for the preparation of pharmaceutical compositions of activity against peptic ulcer and a method for the treatment and prevention of peptic ulcer. The invention also relates to the use of zinc hyaluronate for the prevention of reinfection after the healing of peptic ulcer.

BACKGROUND OF THE INVENTION

The macromolecule known as hyaluronic acid usually occurring in the form of its sodium salt, is a compound known for more than 50 years. It had first been described by Meyer et al [J. Biol. Chem. 107, 629 (1934)]. Hyaluronic acid is a highly viscous native glucosaminoglycan containing alternating β1–3 glucuronic acid and β1–4 glucosamine moieties, its molecular weight is between 50000 and several millions. Hyaluronic acid is found in the connective tissues of all mammals; it occurs in higher levels in the skin, vitreous body of the eye, synovial fluid, umbilical cord as well as cartilaginous tissue.

Up to recently, hyaluronic acid has been employed as the sodium salt in therapy—mainly in ophthalmology, dermatology, surgery, articular therapy—and cosmetics. The salts of hyaluronic acid formed with alkali, alkaline earth, magnesium, aluminum, ammonium and substituted ammonium ions may serve as carriers for promoting the absorption of drugs (see the Belgian patent specification No. 904,547). Heavy metal salts of hyaluronic acid, among these the silver salt, are employed as fungicides; whereas the gold salt is useful for the treatment of rheumatoid arthritis (see the patent specification No. WO 87/05517). However, severe adverse effects of silver and gold compounds are known, i.e. their effects on the immune system, hematopoietic organs and nervous system [M. Shinogi, S. Maeizumi: "Effect of preinduction of metallothionein on tissue distribution of silver and hepatic lipid peroxidation", Biol. Pharm. Bull. (Japan), April 1993 16 (4), p. 372–374; C. Masson et al.: Rev. Med. Interne (France) May-June 1992, 13 (3) p. 225–232 (1992)].

Associates (complexes) of deprotonated hyaluronic acid with 3d metal ions of 4th period of the Periodic Table such as zinc and cobalt hyaluronates with a curative effect especially on crural ulcer, decubitus ulcer or the like are discussed in the Hungarian patent specification No. 203,372, with confirmations by external use.

Now, it has been found that the zinc associate (complex) of hyaluronic acid, i.e. zinc hyaluronate possesses significant gastroprotective activity so it can be used in the prophylaxis and treatment of peptic ulcers including Helicobacter pylori-induced ulcers.

There are known structurally similar gastroprotective compounds in the literature. The anti-gastric ulcer effect of zinc salts of acidic polysaccharides and within these, of mucopolysaccharides is described in the published Japanese patent application No. 60-48950, giving a list of alga-derived agar agaropectin of marine origin, carrageenin, alginic acid as acid polysaccharides; hyaluronic acid, heparin, chondroitin sulfate as mucopolysaccharides; as well as other compounds such as dextran sulfate, carboxymethylcellulose and the like and pectinic acid of plant origin. However, according to this application, the molecular weights of acidic polysaccharides are about a few thousands, preferably about 20 thousand. The zinc salt of hyaluronic acid and its pharmacological activity are not published in the examples at all.

The U.S. Pat. No. 5,514,660 describes the antiulcer effect of pharmaceutical compositions containing an oligosaccharide type active ingredient, together with examples of investigations on the effects of the compounds on the Helicobacter pylori-induced ulcer. Neither hyaluronic acid nor its zinc associate are involved in this specification and no wound-healing effect is mentioned.

Peptic ulcer disease is a complex and multifactorial disease which concerns a great part of civilized population. Many questions still remain in relation to the exact pathogenesis of this disease. In the last five years a new approach has emerged due to the "re-discovery" of Helicobacter pylori. It is generally accepted that the development of peptic ulcer disease in humans is associated with the infection of Helicobacter pylori, but on the other hand H. pylori can not be held responsible for all causes of peptic ulcer. Up to now the peptic ulcer therapy has not changed essentially: still $H_2$ blockers and proton pump inhibitors are the most important requisites of the therapeutic arsenal, whilst the possible therapeutical methods for killing the H. Pylori bacteria are now disclosed in the literature. In addition, the treatment of gastro-duodenal damage caused by nonsteroidal anti-inflammatory drugs has become the center of interest.

A peptic ulcer, developed by any mechanism, may be characterized by an upset of that balance, which exists under healthy conditions between aggressive factors—which induce development of ulcers—and defensive factors—which protect the stomach against induction of ulcers. Thus, an ulcer develops in each case when the aggressive factors are enhanced beyond certain limits and/or the defensive factors become weaker. Defensive factors include the resistance of gastric mucosa, sufficient blood supply of gastric mucosa, and mucus formation [H. Shay: Etiology of peptic ulcer, Am. J. Dig. Dis. 6, 29–49 (1961)]. Among the aggressive factors, the leading ones are the secretion of hydrochloric acid and pepsin as well as all factors stimulating the secretion of any of both substances. The secretion of acid may be enhanced also by a pathological vagal stimulus or increased gastrin formation, by an autoimmune mechanism and in some cases by hormonal effect. In addition, the balance between aggressive and defensive factors may be disturbed also by injuries affecting the whole body. Thus, peptic ulcer is a multifactorial disease. Agents used in ulcer therapy are intended to reduce the role of aggressive factors and/or to enhance the role of defensive factors. Up to recently, the pharmacological investigations have sought ways to weaken the effects of aggressive factors so the primary target was to moderate the acid-pepsin activity. Drugs used in the treatment of ulcer were targeted first to neutralize the acid (antacids such as sodium hydrogen carbonate, or aluminum hydroxide) or to inhibit its secretion ($H_2$ blockers, e.g. cimetidine, famotidine, proton pump inhibitors, e.g. omeprazole); only recently research into those agents which enhance the role of defensive factors became important, beyond the development of a monotherapy useful for killing Helicobacter pylori.

However, compositions strengthening the defensive factors are available only in a limited number and they show some side effects. Such compositions are colloidal bismuth subcitrate (CBS, DeNol), sucralfate and misoprostol. CBS contains bismuth, which is responsible for toxicological problems. Sucralfate a basic aluminum salt of sulphated sucrose possesses some adverse effects, e.g. nausea, vomiting, aluminum intoxication, etc., and the misoprostol, a synthetic prostaglandin analogue, induces an enhanced intestinal activity or nausea.

It can be seen from the above that there is a further need for effective and safe drugs to treat ulcers not accompanied with an increased acid secretion. Such compositions could be employed with success in cases where the aim is to prevent the gastric lesions from the gastric irritative, damaging effect of e.g. nonsteroidal anti-inflammatory drugs such as indomethacin, aspirin by strengthening the mucosal protective mechanism. The number of patients having peptic ulcers due to NSAID (nonsteroidal anti inflammatory drug) consumption might grow in the future if we take into consideration the data showing that more than ten million tablets of nonsteroidal anti-inflammatory drugs are consumed daily worldwide forming the group of most widely used medicaments of today.

The reinforcement of protective mechanism can be important for ulcers caused by Helicobacter pylori infection, too, since the bacteria produce a number of toxins and enzymes (urease, protease, catalase, lipase) damaging the gastric mucosa and giving a free way for the acid and pepsin towards gastric epithelium.

In order to meet the demand described above our aim was to focus on the treatment of peptic ulcer by examining the assumed gastroprotective activity of zinc hyaluronate, a zinc associate (complex) of hyaluronic acid. According to our experimental results, zinc hyaluronate shows a considerable gastroprotective action and seems to be very useful in field of action mentioned above, i.e. in the prevention (prophylaxis) of peptic ulcer formation and/or in the treatment of a developed ulcer, respectively.

OBJECTS OF THE INVENTION

An object of the invention is to provide pharmaceutical compositions with anti-peptic ulcer effect, containing zinc associate (complex) of hyaluronic acid i.e. zinc hyaluronate as active ingredient; as well as to a process for the production thereof by mixing the zinc hyaluronate active ingredient (prepared in a known manner) with therapeutically useful carriers and/or additives and converting the mixture to a pharmaceutical composition.

Another object of the invention is the use of the zinc associate (complex) of hyaluronic acid for the preparation of pharmaceutical compositions with activity against peptic ulcer and a method for the treatment and prevention of peptic ulcer.

SUMMARY OF THE INVENTION

The gastroprotective effect of zinc hyaluronate was verified by various pharmacological investigations. Zinc hyaluronate solutions according to Hungarian patent specification No. 203,372 were used for these examinations. Sodium hyaluronate and zinc chloride, compounds from which zinc hyaluronate was prepared, were also investigated. The molecular weight at the zinc hyaluronate ranges from 500.000 to 1.200.000 daltons.

In pharmacological experiments used to prove the gastroprotective effect of zinc hyaluronate, he investigated how the effectiveness changed with the modification of its molecular weight, and with the various grades of purities. For this purpose, solutions of zinc hyaluronate(I), zinc hyaluronate(II), and zinc hyaluronate (III) with molecular weights of 750.000, 900.000 and 1.200.000, respectively were tested, having the degree of highest purity ("purissimum") in the experiments. Zinc hyaluronate(M) was of "purum" quality degree that is prepared from a low-graded quality material. Our last aim was to make comparison between zinc hyaluronate and one of the most widely used gastroprotectants, sucralfate.

It is evident for a person skilled in the art that, having mixtures of molecules with various degrees of polymerization and molecular weights between very wide limits such as hyaluronic acid compounds, they cannot be characterized by an exact value of molecular weight. In the case of zinc hyaluronate, similarly as with all other hyaluronic acid compounds, "molecular weight" is meant a mean value of molecular weights shown by a mixture of molecules with various degrees of polymerization measured by a given method of molecular weight determination.

The zinc hyaluronate associates of various molecular weights were dissolved in an aqueous solution of 1.0% for the pharmacological experiments. The following example described the preparation's procedure of 1.0% solution of zinc hyaluronate. If not noted otherwise, the percentages mean weight/volume% values.

EXAMPLE 1

Preparation of 1.0% Solution of Zinc Hyaluronate

Sodium hyaluronate (1.0 g) is swollen in 30 ml of water while constant stirring then after adding 18.75 ml of 0.1 molar zinc chloride solution it is filled to 100 ml with distilled water.

The characteristics of sodium hyaluronate used for the preparation of solutions of zinc hyaluronate with various molecular weights and degrees of purity employed in our pharmacological investigations are summarized in the following Table.

|  | characteristics of sodium hyaluronate used for solutions containing | | | |
| --- | --- | --- | --- | --- |
|  | zinc hyaluronate (I) | zinc hyaluronate (II) | zinc hyaluronate (III) | zinc hyaluronate (M) |
| Na-hyaluronate content | 97.77 | 97.50 | 99.07 | 96.25 |
| Molecular weight | 750.000 | 900.000 | 1,200.000 | 982.000 |
| Protein content | 0.018% | 0.032% | 0.019% | 0.16% |
| Viscosity | 14.0 dl/g | 16.0 dl/g | 19.0 dl/g | 17.0 dl/g |
| UV absorption $A^{0.2\%}$ 250 nm | 0.017 | 0.018 | 0.016 | 0.045 |

For the examinations, the employed doses of solutions containing zinc hyaluronate with various molecular weights and degrees of purity, as well as of sodium hyaluronate and zinc chloride solutions were diluted with distilled water and administered in a volume of 10 ml/kg of body weight. The doses of sucralfate used as reference substance as well as indomethacin and powdered charcoal were suspended in 1–2 drops of Tween 80 and diluted to 5 ml/kg of body weight with physiological saline (0.9% by weight/volume of sodium chloride). The doses used of N-ethylmaleimide and N$^G$-nitro-L-arginine methyl ester (L-NAME) were diluted to a volume of 5 ml/kg of body weight. The platelet activating factor (PAF) was dissolved in 0.25% by weight/volume bovine serum albumin prepared with 0.9% by weight/volume sodium chloride solution. The sources of substances employed were as follows.

Zinc hyaluronate (I), (II), (III) and (M) as well as sodium hyaluronate (Gedeon Richter); zinc chloride (Merck); sucralfate (Ulcerlmin$^R$ Chugai); indomethacin (Sigma); N-ethylmaleimide (Fluka); N$^G$-nitro-L-arginine methyl ester (Sigma); L-arginine (free base) (Sigma); D-arginine (free base) (Sigma); bovine serum albumin (Sigma); charcoal (Sigma).

The pharmacological activity of the zinc hyaluronate associate was studied by using the following methods.

1. Inhibition of Acidified-ethanol Induced Gastric Lesions

Female RG-Wistar rats weighing between 120–150 g were used. Before experiments animals were fasted for 24 hours but received water ad libitum.

Experiments were carried out according to the technique similar to that described by A. Robert [Gastroenterology 77, 7661 (1979)].

Acidified ethanol (mixture of 50 ml of abs. ethanol and 1 ml of concentrated HCl) was used as strong irritants. Dose of acidified ethanol was 0.5 ml/100 g body weight with intragastric administration. Test compounds were given orally 30 minutes before the acidified ethanol challenge. When the duration of action of test compound was studied test material was administered 60 or 120 minutes earlier to the irritating effect induced by acidified-ethanol effect. One hour after the acidified ethanol treatment rats were sacrificed by cervical dislocation. Stomachs were removed and opened along the greater curvature and mildly washed down. The longitudinal hemorrhagic lesions were assayed by length.

$ED_{50}$ value was defined as the dose that gave a 50% decrease in ulcer index.

To study the mechanism of action of the compound to be tested, the involvement of endogenous NO in the development of acidified-ethanol induced gastric damage was also studied by intraperitoneal administration of L-N$^G$-nitroarginine methyl ester (L-NAME). L-NAME at a dose of 25 mg/kg was injected 15 minutes before the test compound. In subsequent experiments the test compound (p.o.), L-NAME (25 mg/kg i.p.), L-arginine (400 mg/kg i.v.) were administered 30, 45 or 60 minutes before oral administration of acidified-ethanol.

The results are summarized in the following Tables. The control group shown in the Tables received only vehicle (distilled water) instead of zinc hyaluronate.

TABLE 1

Effect of zinc hyaluronate (I) on acidified ethanol induced gastric lesion

|  | N | Dose mg/kg p.o. | Lesion length/stomach | Inhibition % |
|---|---|---|---|---|
| Control | 12 | — | 82.4 ± 11.5 | — |
|  | 6 | 1 | 95.3 ± 14.8 | 0 |
|  | 13 | 10 | 53.6 ± 7.3* | 35.0 |
| Zinc | 7 | 50 | 27.4 ± 7.6* | 66.7 |
| hyaluronate (I) | 13 | 100 | 5.4 ± 2.0* | 93.4 |

*p < 0.05 compared with the control group
$ED_{50}$ = 15.9 mg/kg/10 ml p.o.

TABLE 2

Effect of zinc hyaluronate (II) on acidified ethanol induced gastric lesion

|  | N | Dose mg/kg p.o. | Lesion length/stomach mm ± S.E.M. | Inhibition % |
|---|---|---|---|---|
| Control | 21 | — | 83.7 ± 7.3 | — |
|  | 13 | 10 | 48.0 ± 10.9* | 42.7 |
|  | 6 | 25 | 19.0 ± 4.4* | 77.3 |
| Zinc hyaluronate (II) | 8 | 50 | 13.3 ± 4.8* | 84.1 |
|  | 8 | 100 | 1.6 ± 0.5* | 98.1 | p < 0.0 *5 compared with the control group
$ED_{50}$ = 11.1 mg/kg/10 ml p.o.

TABLE 3

Effect of zinc hyaluronate (III) on acidified ethanol induced gastric lesion

|  | N | Dose mg/kg p.o. | Lesion length/stomach mm ± S.E.M. | Inhibition % |
|---|---|---|---|---|
| Control | 14 | — | 69.4 ± 12.8 | — |
|  | 14 | 10 | 98.4 ± 12.7 | 0 |
|  | 7 | 25 | 43.7 ± 7.7 | 37.0 |
| Zinc hyaluronate (III) | 13 | 50 | 14.9 ± 4.5* | 78.5 |
|  | 8 | 100 | 9.9 ± 3.5* | 85.7 |

*p < 0.05 compared with the control group
$ED_{50}$ = 33.18 mg/kg/10 ml p.o.

TABLE 4

Effect of zinc hyaluronate (M) on acidified ethanol induced gastric lesion

|  | N | Dose mg/kg p.o. | Lesion length/stomach mm ± S.E.M. | Inhibition % |
|---|---|---|---|---|
| Control | 18 | — | 110.7 ± 16.0 | — |
|  | 18 | 10 | 57.9 ± 8.2* | 47.7 |
|  | 6 | 25 | 33.3 ± 7.7* | 69.9 |
| Zinc | 6 | 50 | 13.0 ± 3.0* | 88.3 |
| hyaluronate (M) | 6 | 100 | 2.7 ± 1.4* | 97.6 |

*p < 0.05 compared with the control group
$ED_{50}$ = 10.4 mg/kg/10 ml p.o. −30 minutes

TABLE 5

Effect of sodium hyaluronate on acidified ethanol induced gastric lesion

|  | N | Dose mg/kg p.o. | Lesion length/stomach mm ± S.E.M. | Inhibition % |
|---|---|---|---|---|
| Control | 18 | — | 77.8 ± 10.3 | — |
| Sodium | 18 | 50 | 65.7 ± 9.8 | 15.6 |
| hyaluronate | 18 | 100 | 49.9 ± 6.0* | 35.9 |

*p < 0.05 compared with the control group

TABLE 6

Effect of zinc chloride on acidified ethanol induced gastric lesion

|  | N | Dose mg/kg p.o. | Lesion length/stomach mm ± S.E.M. | Inhibition % |
|---|---|---|---|---|
| Control | 10 | — | 51.5 ± 13.8 | — |
|  | 10 | 3.2 | 29.0 ± 4.0 | 43.7 |
| Zinc chloride | 10 | 6.4 | 24.7 ± 7.7 | 52.0 |
|  | 10 | 12.8 | 6.7 ± 1.6* | 87.0 |

*p < 0.05 compared with the control group
$ED_{50}$ = 4.5 mg/kg/10 ml p.o. −30 minutes

TABLE 7

Effect of sucralfate on the gastric necrosis induced by acidic ethanol

|  | N | Dose mg/kg p.o. | Lesion length/stromach mm ± S.E.M. | Inhibition % |
|---|---|---|---|---|
| Control | 4 | — | 60.8 ± 14.6 | — |
|  | 4 | 50 | 64.0 ± 25.9 | 0 |
| Sucralfate | 4 | 100 | 15.0 ± 5.5* | 75.3 |
|  | 4 | 400 | 7.5 ± 3.0* | 87.7 |

*$p < 0.05$ compared with the control group
$ED_{50} = 112.2$ mg/kg/p.o.

TABLE 8

Effect of zinc hyaluronate (M) on acidified ethanol induced gastric lesion after increasing the pretreatment time to 60 minutes

|  | N | Dose mg/kg p.o. | Lesion length/stromach mm ± S.E.M. | Inhibition % |
|---|---|---|---|---|
| Control | 18 | — | 69.7 ± 7.1 | — |
|  | 11 | 25 | 49.7 ± 5.9 | 28.7 |
| Zinc hyaluronate (M) | 12 | 50 | 37.9 ± 12.2* | 45.6 |
|  | 12 | 100 | 4.6 ± 1.7* | 93.4 |

*$p < 0.05$ compared with the control group
$ED_{50} = 44.1$ mg/kg/10 ml p.o. −60 minutes

TABLE 9

Effect of zinc hyaluronate (M) on acidified ethanol induced gastric lesion after increasing the pretreatment time to 120 minutes

|  | N | Dose mg/kg p.o. | Lesion length/stromach mm ± S.E.M. | Inhibition % |
|---|---|---|---|---|
| Control | 12 | — | 60.6 ± 7.4 | — |
|  | 12 | 25 | 53.2 ± 7.7 | 12.2 |
| Zinc hyaluronate (M) | 12 | 50 | 32.8 ± 7.5* | 45.9 |
|  | 12 | 100 | 10.3 ± 4.6* | 83.0 |

$p < 0.05$ compared with the control group
$ED_{50} = 53.0$ mg/kg/10 ml p.o. −120 minutes

TABLE 10

Effect of $N^G$-nitro-L-arginine methyl ester (L-NAME) on the protective action of zinc hyaluronate (M) (ZH/M) against acidified ethanol induced gastric damage

|  | N | Dose mg/kg/p.o. | Lesion length/ stomach mm ± S.E.M. | Inhibition[a] % |
|---|---|---|---|---|
| Vehicle + Vehicle | 20 | 0 + 0 | 60.5 ± 6.8 | — |
| Vehicle + ZH/M | 20 | 0 + 50 | 18.4 ± 2.3* | 69.6 |
| L-NAME + ZH/M | 20 | 25 + 50 | 41.2 ± 4.6*b | 31.9 |
| L-Arg + L-NAME + ZH/M | 21 | 400 + 25 + 50 | 24.1 ± 4.4*c | 60.2 |
| D-Arg + L-NAME + ZH/M | 21 | 400 + 25 + 50 | 31.2 ± 3.5*d | 48.4 |

[a]compared with the vehicle + vehicle group
*$p < 0.05$ compared with the vehicle + vehicle group
b$p < 0.05$ compared with the vehicle + ZH/M group
c$p < 0.05$ compared with the L-NAME + ZH/M group
d$p < 0.05$ compared with the vehicle + ZH/M group

TABLE 11

Effect of $N^G$-nitro-L-arginine methyl ester (L-NAME) on the protective action of zinc chloride against acidified ethanol induced gastric damage

|  | N | Dose mg/kg p.o. | Lesion length/ stomach mm ± S.E.M. | Inhibition* % |
|---|---|---|---|---|
| Vehicle + vehicle | 23 | 0 + 0 | 74.3 ± 13.5 | — |
| Vehicle + zinc chloride | 22 | 0 + 25 | 8.0 ± 2.6* | 89.2 |
| L-NAME + zinc chloride | 22 | 25 + 25 | 19.9 ± 5.5* | 73.2 |

[a]compared with the vehicle + vehicle group
*$p < 0.05$ compared with the vehicle + vehicle group It can be observed from the results shown in Tables 1, 2, 3 and 4 that zinc hyaluronate of various molecular weights and purities possess a significant gastroprotective effect: after oral administration. The compound inhibits in a dose-dependent manner the formation of acidified ethanol induced gastric damage. The $ED_{50}$ values of various zinc hyaluronates were: zinc hyaluronate(I): 15.9 mg/kg; zinc hyaluronate(II): 11.1 mg/kg; zinc hyaluronate(III): 33.2 mg/kg; and zinc hyaluronate(M): 10.4 mg/kg. In opposition to the zinc hyaluronate associates (I), (II), (III) and (M), sodium hyaluronate given in a 100 mg/kg oral dose exerted a protective action of only 36% on acidified ethanol induced gastric lesion (Table 5). The $ED_{50}$ value related to zinc chloride is 4.5 mg/kg after oral administration (Table 6). Sucralfate, a known cytoprotective agent used as reference compound showed a weaker activity (with an $ED_{50}$ value of 112 mg/kg) than the tested zinc hyaluronates did (Table 7).

The duration of the effect was investigated on the zinc hyaluronate associate(M). Increasing the pretreatment time the $ED_{50}$ value rose (Tables 8 and 9). It can be seen from the results that the zinc hyaluronate(M) does not bind to the gastric mucosa in an irreversible manner.

The connection between the cytoprotective effect of zinc hyaluronate and endogenic NO was studied by using an inhibitor of the nitrogen(II) oxide biosynthesis namely, $N^G$-nitro-L-arginine methyl ester (L-NAME). Considering that zinc hyaluronate(II) and zinc hyaluronate(M) had shown the same activity in acidified ethanol test, the latter was the only one tested in this experiment.

It is obvious from our results (Table 10) that a pretreatment by L-NAME considerably reduced the gastroprotective activity of zinc hyaluronate(M); this was suspended by the pretreatment with L-arginine but was not abolished by pretreatment with D-arginine. On the other hand, the protective effect of zinc chloride was not influenced by a pretreatment with L-NAME in this test (Table 11). Sodium hyaluronate was not tested against L-NAME because the gastroprotective effect of this substance was so mild (Table 5) that the results can not be evaluated exactly. The phenomenon, that the protective effect of zinc hyaluronate is significantly decreased by L-NAME, whereas that of zinc chloride is not affected, seems to prove that NO might play a role in the development of cytoprotective effect of zinc hyaluronate(M).

2. Inhibition of Indomethacin Induced Gastric Lesion

Female RG Wistar rats weighing between 120–150 g were used. Before the experiments animals were fasted for 24 hours but received water ad libitum. Test compounds were given orally, 30 minutes later the animals were treated subcutaneously with indomethacin at a dose of 40 mg/kg. Four hours after the irritating indomethacin administration the animals were killed by cervical dislocation. The stomachs were removed, opened along the greater curvature and the hemorrhagic lesions were counted on the glandular stomach.

$ED_{50}$ value represents the dose which protects the stomach by 50 % from the damaging effect of indomethacin.

The results are shown in the following Tables. The control group shown in the Tables received only vehicle (distilled water) instead of zinc hyaluronate.

TABLE 12

Effect of zinc hyaluronate (I) on indomethacin induced gastric lesion

|  | N | Dose mg/kg p.o. | lesion number/ stomach ± S.E.M. | Inhibition % |
|---|---|---|---|---|
| Control | 6 | — | 8.3 ± 2.1 | — |
|  | 6 | 1.0 | 4.7 ± 2.1 | 43.4 |
| Zinc hyaluronate (I) | 6 | 10.0 | 3.7 ± 1.9 | 55.4 |
|  | 6 | 100.0 | 0.8 ± 0.4* | 90.4 |

*p < 0.05 compared with the control group
$ED_{50}$ = 2.8 mg/kg/10 ml p.o.

TABLE 13

Effect of zinc hyaluronate (II) on indomethacin induced gastric lesion

|  | N | Dose mg/kg p.o. | Lesion number/ stomach ± S.E.M. | Inhibition % |
|---|---|---|---|---|
| Control | 14 | — | 12.9 ± 2.7 | — |
| Zinc hyaluronate (II) | 14 | 1.0 | 8.8 ± 2.1 | 31.8 |
| Control | 14 | — | 17.0 ± 3.3 | — |
| Zinc hyaluronate (II) | 14 | 10.0 | 7.4 ± 1.9* | 56.5 |
|  | 7 | 100.0 | 3.7 ± 0.8* | 78.2 |

*p < 0.05 compared with the control group
$ED_{50}$ = 5.79 mg/kg/10 ml p.o.

TABLE 14

Effect of zinc hyaluronate (III) on indomethacin induced gastric lesion

|  | N | Dose mg/kg p.o. | Lesion number/ stomach ± S.E.M. | Inhibition % |
|---|---|---|---|---|
| Control | 7 | — | 18.4 ± 3.4 | — |
|  | 7 | 1.0 | 17.0 ± 4.5 | 7.6 |
| Zinc hyaluronate (III) | 7 | 10.0 | 7.9 ± 2.5* | 57.6 |
|  | 7 | 100.0 | 3.0 ± 1.4* | 83.7 |

*p < 0.05 compared with the control group
$ED_{50}$ = 10.2 mg/kg/10 ml p.o.

TABLE 15

Effect of zinc hyaluronate (M) on indomethacin induced gastric lesion

|  | N | Dose mg/kg p.o. | Lesion number/ stomach ± S.E.M. | Inhibition % |
|---|---|---|---|---|
| Control | 24 | — | 18.5 ± 2.9 | — |
|  | 18 | 1.0 | 15.6 ± 6.2 | 15.7 |
| Zinc hyaluronate (M) | 12 | 10.0 | 5.9 ± 1.9* | 68.1 |
|  | 6 | 100.0 | 2.0 ± 0.9* | 89.2 |

*p < 0.05 compared with the control group
$ED_{50}$ = 6.2 mg/kg/10 ml p.o.

TABLE 16

Effect of sodium hyaluronate and zinc chloride on indomethacin induced gastric lesion

|  | N | Dose mg/kg p.o. | Lesion number/stomach ± S.E.M. | Inhibition % |
|---|---|---|---|---|
| Control | 18 | — | 22.9 ± 3.1 | — |
| Sodium hyaluronate | 18 | 100 | 14.6 ± 3.3 | 36.2 |
| Control | 12 | — | 12.2 ± 3.6 | — |
| Zinc chloride | 11 | 25 | 15.1 ± 3.7 | 0 |

TABLE 17

Effect of sucralfate on indomethacin induced gastric lesion

|  | N | Dose mg/kg p.o. | Lesion number/stomach ± S.E.M. | Inhibition % |
|---|---|---|---|---|
| Control | 11 | — | 16.9 ± 3.4 | — |
|  | 11 | 40 | 14.4 ± 4.8 | 14.8 |
| Sucralfate | 11 | 80 | 6.4 ± 2.2* | 62.1 |
|  | 11 | 160 | 2.9 ± 1.4* | 82.8 |

*p < 0.05 compared with the control
$ED_{50}$ = 74.9 mg/kg p.o.

It can be seen from the results that zinc hyaluronates (I), (II), (III) and (M) are effective on indomethacin-induced gastric lesion (Tables 12, 13, 14 and 15). It is also evident from the results that zinc hyaluronates inhibit development of indomethacin induced gastric lesions in a dose-depending manner. After oral administration their $ED_{50}$ values are: 2.8 mg/kg, 5.8 mg/kg, 10.2 mg/kg and 6.2 mg/kg, respectively (see Tables 12, 13, 14 and 15).

It is obvious from the data of Table 16 that sodium hyaluronate and zinc chloride do not provide any effect to protect the gastric mucosa against the damaging action of indomethacin. Furthermore, it can be seen from the higher $ED_{50}$ value (74.9 mg/kg) of sucralfate (Table 17) that the protective action of zinc hyaluronate exceeds the effect of sucralfate.

3. Inhibition of the Stress Induced Gastric Lesions

Female RG Wistar rats weighing between 120–150 g were used. Before the experiments animals were fasted for 24 hours but received water ad libitum. Experiments were carried out according to the technique similar to that described by Senay et al., (1967). [Proc. Soc. Exp. Biol. Med.124,1221, (1967)].

Based on the results of acidified ethanol tests, where zinc hyaluronate (II) and zinc hyaluronate (M) proved to have identical activity, zinc hyaluronate (M) was only studied in the stress model.

Test compounds were given orally. 30 minutes later the animals were immobilized in plastic restraint boxes then placed into a refrigerator at 4° C.–8° C. temperature. Four hours later the animals were removed from both the refrigerator and the restraint boxes and one hour later they were sacrificed by cervical dislocation. The stomachs were removed, opened along the greater curvature and hemorrhagic lesions were scored by a zero to 3 scale: stomachs free from any damage were given a score of 0, stomachs with only a few hemorrhagic lesion were given a score of 1, stomachs with more lesion numbers than 10 were given a score of 2, and stomachs with a lot of lesions were characterized with a score of 3.

The $ED_{50}$ were defined as the dose needed to decrease the score of gastric lesions by 50%. The results can be observed in the following Tables.

TABLE 18

Effect of zinc hyaluronate (M) on stress-induced gastric lesion

| | N | Dose mg/kg p.o. | Lesion score/stomach ± S.E.M. | Inhibition % |
|---|---|---|---|---|
| Control | 10 | — | 1.7 ± 0.4 | — |
| | 5 | 25 | 1.0 ± 0.3 | 41.2 |
| Zinc hyaluronate (M) | 5 | 50 | 0.4 ± 0.2* | 76.5 |
| | 5 | 100 | 0* | 100 |

*p <0.05 compared with the control group
$ED_{50}$ = 29.4 mg/kg/10 ml p.o. - 30 minutes

TABLE 19

Effects of sodium hyaluronate and zinc chloride on stress-induced gastric lesion

| | N | Dose mg/kg p.o. | Lesion score/stomach ± S.E.M. | Inhibition % |
|---|---|---|---|---|
| Control | 30 | — | 1.5 ± 0.2 | — |
| Sodium hyaluronate | 29 | 100 | 0.9 ± 0.2* | 40.0 |
| Zinc chloride | 29 | 25 | 0.6 ± 0.2* | 40.0 |

Various stress situations, such as cold and considerable restriction of movement induce acute gastric damage in rats. It can be seen from the results, that the cold-restraint stress was prevented by zinc hyaluronate (M) in a dosedependent manner with $ED_{50}$=29.4 mg/kg in the case of oral administration. (Table 18). On the other hand sodium-hyaluronate and zinc chloride had only slight protective effects on cold-restraint induced gastric damage. (Table 19).

4. Inhibition of the Gastric Damage Induced by the Platelet Activating Factor (PAF)

Male, RG-Wistar rats weighing between 200–250 g were used. Before the experiments animals were fasted for 24 hours but received water ad libitum. Experiments were carried out according to the technique similar to that described by Wallace and Whittle (1986). [Br.J.Pharmac., 89,415, (1986)]. Animals were anaesthetized by intraperitoneal administration of urethane at a dose of 1 g/kg in a volume of 10 ml/kg. Femoral vein was then prepared and cannulated for administration of ulcerogenic PAF. After the surgery PAF was infused intravenously at a rate of 0.1 ml/min for ten minutes at a dose of 200 ng/kg/min. Test compounds were given 30 minutes before the PAF challenge. One hour after the infusion of PAF animals were sacrificed by cervical dislocation; their stomachs were removed and opened along the greater curvature. The hemorrhagic erosions were evaluated by a zero to three scoring system. Stomachs free from any damage were characterized by a score of zero, stomachs with only a few, little change from normal were given a score of 1, stomachs with a moderate damage were characterized by a score of 2, and stomachs with severe, diffuse hyperaemia and/or haemorrhagia were given a score of 3.

PAF (platelet activating factor) is an endogenous phospholipid which has nowadays been described as the most potent gastric ulcerogen. Its endogenic release may play a role in the development of certain forms of peptic ulcer [Rosam et al. (1986); Wallace et al. (1986)].

The results are illustrated in the following Table 20.

TABLE 20

Effect of zinc hyaluronate (M), sodium hyaluronate and zinc chloride, on platelet activating factor (PAF) induced gastric lesion

| | N | Dose mg/kg p.o. | Lesion score/stomach ± S.E.M. | Inhibition % |
|---|---|---|---|---|
| Control | 32 | — | 2.2 ± 0.1 | — |
| Zinc hyaluronate (M) | 5 | 50 | 1.6 ± 0.4 | 27.3 |
| | 15 | 100 | 1.3 ± 0.2* | 40.9 |
| Sodium hyaluronate | 5 | 100 | 2.6 ± 0.2$^a$ | 0 |
| Zinc chloride | 15 | 25 | 1.7 ± 0.2$^b$ | 22.7 |

*p < 0.05 compared with the control group
$^a$p < 0.05 compared with the zinc hyaluronate (M) 100 mg/kg group
$^b$p < 0.05 compared with the sodium hyaluronate group According to those described for the stress model, only zinc hyaluronate (M) was tested in the PAF-induced model. The zinc hyaluronate (M) strongly reduced the ulcerogenic effect of PAF, whereas sodium hyaluronate did not show such effect. Zinc chloride exhibited some protective action against PAF; this was, however, much less than that of the zinc hyaluronate associate (Table 20).

5. Inhibition of Acetic Acid Induced Chronic Qastric Ulcer

Female, RG Wistar rats weighing between 120–150 g were used. Before the surgery animals were deprived of food for 24 hours but received water ad libitum.

The chronic gastric ulcer was induced by the injection of 25 μl/animal of 20% (v/v) acetic acid into the gastric wall under light ether anaesthesia according to the method similar to that described by Takagi et al. (1969). The oral treatment with the test compounds was started five days after the surgery and continued in a once-a-day regimen up to the 14th day. The animals were killed on the 15th day and their stomachs were dissected. The severity of ulceration was evaluated by the measurement of the diameter of the ulcers and the area affected was calculated.

The healing effect was expressed as differences in percentage between the control and test group values.

Acetic acid irritates the stomach wall and causes a well defined ulcer, which is very similar to the human ulcer both in its form as well as in its microscopical picture. The results are illustrated in the following Tables.

TABLE 21

Effect of zinc hyaluronate (II) on acetic acid induced chronic gastric ulcer

| | N | Dose mg/kg p.o. | Ulcerated area mm$^2$ ± S.E.M. | Effect on healing % |
|---|---|---|---|---|
| Control | 27 | — | 8.9 ± 1.2 | — |
| | 10 | 0.01 | 6.2 ± 1.0 | 30.3↑ |
| | 10 | 0.1 | 5.8 ± 1.1 | 34.8↑ |
| Zinc hyaluronate (II) | 10 | 1.0 | 3.7 ± 1.6* | 58.4↑ |

↑healing slowed down
*p < 0.05 compared with the control group

TABLE 22

Effects of zinc hyaluronates of different molecular weight on acetic acid induced chronic gastric ulcer

|  | N | Dose mg/kg p.o. | Ulcerated area mm$^2$ ± S.E.M. | Effect on healing |
|---|---|---|---|---|
| Control | 9 | — | 9.2 ± 1.6 | — |
| Zinc hyaluronate (I) | 10 | 1.0 | 10.0 ± 2.3 | 8.8↓ |
| Control | 27 | — | 8.9 ± 1.2 | — |
| Zinc hyaluronate (II) | 10 | 1.0 | 3.7 ± 0.6* | 58.4↑ |
| Control | 9 | — | 9.2 ± 1.6 | — |
| Zinc hyaluronate (III) | 10 | 1.0 | 6.8 ± 0.8 | 26.1↑ |

↓ healing slowed down
↑ healing accelerated

TABLE 23

Effect of Sucralfate on acetic acid induced gastric ulcer

|  | N | Dose mg/kg p.o. | Ulcerated area mm$^2$ ± s.e.m. | Effect on healing % |
|---|---|---|---|---|
| Control | 9 | — | 5.7 ± 1.2 | — |
| Sucralfate | 10 | 100 | 6.7 ± 1.5 | 18.0↓ |
| Control | 10 | — | 9.2 ± 1.6 | — |
| Sucralfate | 10 | 500 | 4.3 ± 1.3* | 53.0↑ |

↓ healing slowed down
↑ healing accelerated
$p < 0.05$ compared with the control group

TABLE 24

Effect of zinc hyaluronate (M) on acetic acid induced chronic gastric ulcer

|  | N | Dose mg/kg p.o. | Ulcerated area mm$^2$ ± S.E.M. | Effect on healing % |
|---|---|---|---|---|
| Control | 10 | — | 12.9 ± 2.5 | — |
|  | 10 | 0.1 | 9.4 ± 2.3 | 27.1↑ |
| Zinc-hyaluronate (M) | 9 | 1.0 | 7.6 ± 1.4 | 41.1↑ |

↑ healing accelerated

Zinc hyaluronate(II) accelerated the healing of chronic gastric ulcer induced by acetic acid (Table 21). A significant ($p<0.005$) change was observed at a dose of 1 mg/kg; however, not a negligible curative effect was measured even with a dose 0.01 mg/kg. Neither zinc hyaluronate(I), nor zinc hyaluronate(III) had any effect on chronic ulcer healing at a dose of 1.0 mg/kg (Table 22)

The reference sucralfate was also less effective in accelerating the gastric ulcer healing than the zinc hyaluronate(II) as it is shown in Table 23. The dose of sucralfate had to be increased to 500 mg/kg to achieve an enhancement of 53% in the curative effect.

Figure 1:
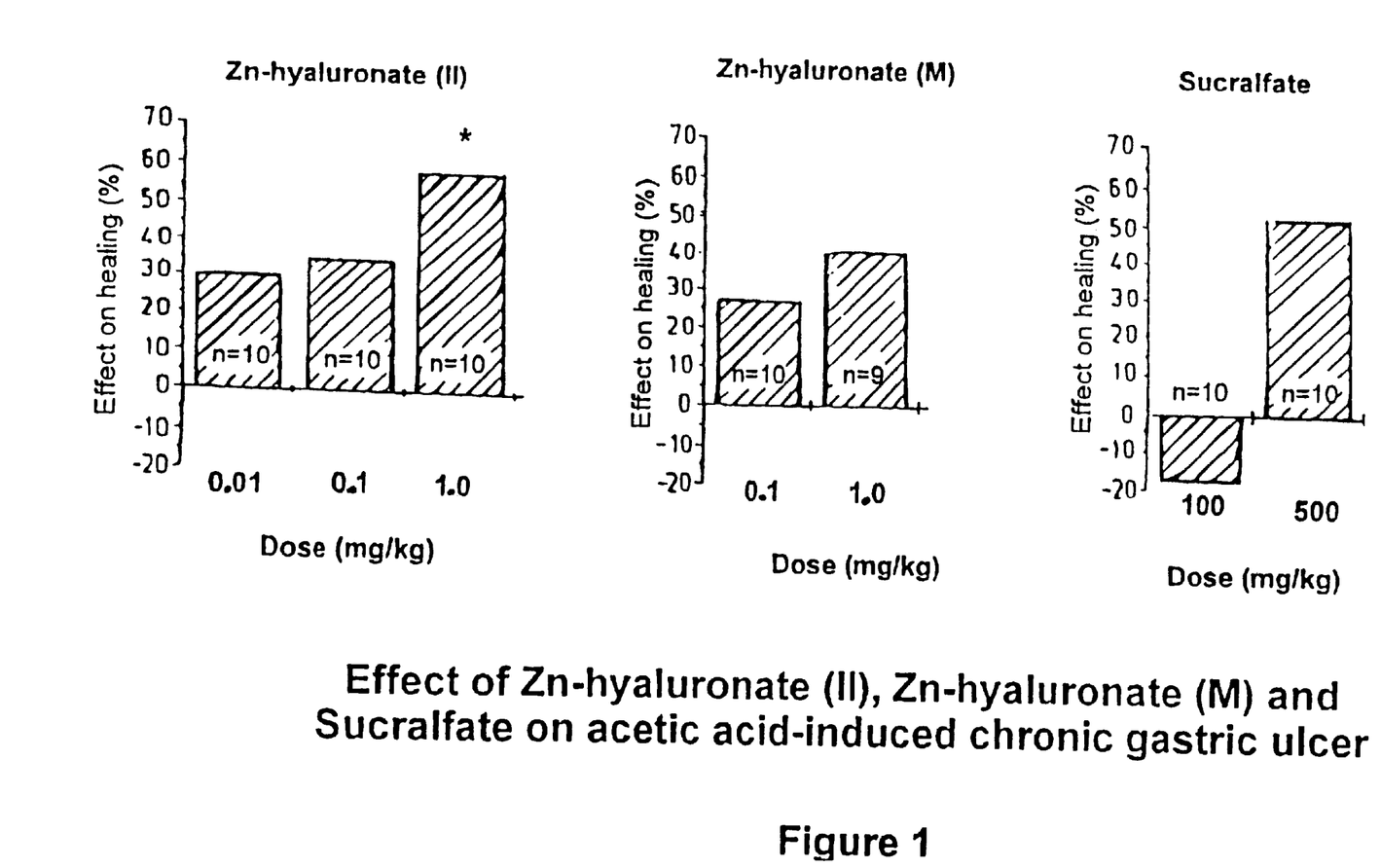
FIG. 1 is a series of bar graphs comparing at specified dosages the healing effect of Zn hyaluronate (E), zinc hyaluronate (M) and sucralfate on acetic acid-induced chronic gastric ulcer.

Zinc hyaluronate (M) also accelerated the healing of acetic acid induced ulcer, however, the accelerating effect was less pronounced than that of zinc hyaluronate(II). Zinc hyaluronate (M) also exerts its maximum activity at a dose of 1 mg/kg, a result confirming our observation discussed above i.e. that the effects of zinc hyaluronates of various origin are not significantly different from each other (Table 24 and FIG. 1).

6. Inhibition of Indomethacin Induced Intestinal Ulcer

Female, RG-Wistar, non-fasted rats weighing between 120–150 g were used. The intestinal ulcer was induced by oral administration of 15 mg/kg indomethacin. Test compound was given to animals orally 3 times over 48 hours in 24 hour equal intervals. The first introduction of test compound preceded the single indomethacin treatment by 60 minutes. Animals were killed 72 hours after the first administration of the test compound. Control animals received vehicle instead of test compound and normal rats mean non-fasted, non-treated rats.

The small intestine segment from pylorus to cecum was removed, placed into 0.9% (w/v) sodium chloride solution at 37° C. and it was connected with a BP recorder through one of its ends via a polyethylene cannula. After ligating both ends of the prepartum the pressure was increased inside the intestine until air bubbles appeared at the weakened site of the intestinal wall. This pressure is expressed in Hgmm and is denoted tensile strength (TS). The results are shown in the following Table 25.

TABLE 25

Effect of zinc hyaluronate (II) on indomethacin induced intestinal ulcer

|  | N | Dose mg/kg p.o. | Tensile strength of intestinal wall as index of ulceration Hgmm ± S.E.M. |
|---|---|---|---|
| Normal | 7 | — | 227.1 ± 7.6 |
| Control | 18 | vehicle | 16.7 ± 6.0 |
|  | 7 | 3 × 1 | 27.9 ± 8.9 |
| Zinc hyaluronate (II) | 8 | 3 × 10 | 41.3 ± 10.9* |
|  | 8 | 3 × 100 | 48.8 ± 11.3* |

*$p < 0.05$ compared with the control group

It appears from the experimental results that zinc hyaluronate (II) had a protective effect on the intestinal wall against ulceration induced by indomethacin. At doses of 10 mg/kg and 100 mg/kg the tensile strength of intestinal wall increased by almost three times compared to the control group. The increase of tensile strength, however was not accompanied by a considerable decrease in ulceration (Table 25).

7. Inhibition of the Gastrointestinal Motility in the Charcoal Propulsion Test

In addition to examinations of zinc hyaluronates on various acute and chronic models, it was studied if this substance could exert any effect on the gastrointestinal motility.

Experiments were performed on female, RG-Wistar rats weighing 120–140 g, which were fasted for 24 hours but received water ad libitum.

The experimental procedure was carried out according to the technique similar to that described of P. A. Janssen and A. J. Jageneau [J. Pharm. Pharmacel. 9, 381 (1957)].

Test compounds were given orally at a dose of 100 mg/kg. Control animals received physiological saline solution instead of test compounds. 30 minutes later, the 5% (w/v) charcoal suspension was administered orally at a volume of 0.5 ml/animal. 60 minutes after the charcoal treatment the animals were sacrificed by cervical dislocation. The intestine from pylorus to cecum was removed, its lengths measured along with the distance traversed by the charcoal meal.

Motility was expressed as the ratio of length of charcoal suspension to the length of the whole intestine. The results are shown in the following Tables.

TABLE 26

Effects of zinc hyaluronates (I), (II) and (III) on gastrointestinal motility

| | N | Dose mg/kg p.o. | Length of intestine mm ± S.E.M. | Propulsion of charcoal suspension mm ± S.E.M. | Ratio** |
|---|---|---|---|---|---|
| Control | 5 | — | 766 ± 2.0 | 604 ± 3.1 | 0.79 ± 0.04 |
| Zink-hyaluronate (I) | 5 | 100 | 916 ± 3.4 | 718 ± 5.6 | 0.79 ± 0.07 |
| Zink-hyaluronate (II) | 5 | 100 | 792 ± 2.7 | 610 ± 3.9 | 0.77 ± 0.04 |
| Zink-hyaluronate (III) | 5 | 100 | 768 ± 3.8 | 68 ± 2.5 | 0.89 ± 0.03* |

*p < 0.05 compared with the control group
**ratio of charcoal suspension to the whole intestinal part

TABLE 27

Effect of zinc hyaluronate (M) on gastrointestinal motility

| | N | Dose mg/kg p.o. | Length of intestine mm ± S.E.M. | Propulsion of charcoal suspension mm ± S.E.M. | Ratio** |
|---|---|---|---|---|---|
| Control | 6 | — | 782 ± 2.3 | 688 ± 4.0 | 0.88 ± 0.03 |
| Zinc hyaluronate (M) | 6 | 100 | 788 ± 2.5 | 655 ± 3.9 | 0.83 ± 0.03 |

**ratio of charcoal suspension to the whole intestinal part

It can be seen from the results of investigations (Tables 26 and 27) that neither zinc hyaluronate (I) and (II) nor zinc hyaluronate (M) have any effect on the intestinal motility: the absence of change in activity demonstrates that they do not stick to the gastric mucosa irreversibly and on the other hand they do not irritate the intestine to make it hyperactive.

Having compared the efficacy of zinc hyaluronates with different molecular weight on some of the ulcer-tests it was surprisingly found that a definite relation exists between gastroprotective action and molecular weight. It can be seen from the previous experiments that the highest affectivity of zinc hyaluronate having different molecular weight in a range of 700.000 and 1.200.000 dalton appears at a molecular weight of about 900.000 dalton. A further increase of molecular weight is not accompanied by an enhancement of effect. Our conclusion from this experimental observation is that the molecular weight has a prominent role in achieving the optimum effect.

Study of the Affectivity Against Helicobacter Pylori Bacteria

These experiments were performed on Helicobacter pylori strains cultivated from the gastric biopsy samples of patients suffering from various ulcers. An 1% by (w/w) solutions of De-Nol (colloidal bismuth subcitrate) was used as reference substance. An agar medium supplemented with 10% of bovine blood was employed. Plates containing no substance to be tested were used as controls. The plates inoculated were incubated at 37° C. in a gas atmosphere containing 5% of oxygen and 7–8% of carbon dioxide for 3–5 days.

Minimum inhibitory concentration (MIC) value was considered to be the lowest concentration of substances totally inhibiting the growth (propagation) of well-propagating bacteria on control plates. The MIC values of zinc hyaluronate associate and De-Not measured on the strains investigated are shown in the following Table.

| Sign of strain | Zinc hyaluronate MIC μg/ml | De-Nol MIC μg/ml |
|---|---|---|
| 822/96 | 500 | 500 |

It appears from data of the above table that the in vitro activity of zinc hyaluronate against Helicobacter pylori is commensurable with activity of De-Nol used in therapeutics. This fact is remarkable since De-Nol is a bismuth-containing composition with not negligible side effects (toxicity problems; its ingestion is unpleasant for the patient) whereas such side effects may not be expected by using the zinc hyaluronate associate.

Conclusions

The present study demonstrates that zinc hyaluronates with various molecular weights have considerable gastroprotective activities. Their anti-ulcer effects were investigated on several acute and chronic gastric ulcer models and were compared in most of the cases with a well-known gastroprotective drug, sucralfate.

The results confirmed that all types of zinc hyaluronates are potent cytoprotective agents as they prevented the gastric mucosa against the damaging effect of acidified-ethanol. From the results it can be concluded that zinc hyaluronates having molecular weight between 700.000 and 1.200.000 daltons, are effective cytoprotectants regardless of the quality of raw material ("purum" or "puriss") used for their preparation. The maximum of the effectiveness is at a molecular weight of 900.000 daltons.

By increasing the pretreatment time the cytoprotective effect is reduced only to a small extent, a fact indicating the prolonged activity, which is not accompanied by undesired, irreversible alterations. Our experiments intended to elucidate the mechanism of action—which have been carried out only on "purum" quality of zinc hyaluronate based on those said above—seem to confirm that zinc hyaluronate exerts its gastroprotective action through a mechanism, which is neither characteristic of zinc chloride nor sodium hyaluronate. It was aimed to make clear this mechanism by examining the role of endogenic NO. The experiments showed that NO is likely to play a role in the development of cytoprotective effect of zinc hyaluronate. This is important since growing attention is devoted recently to a possible relation between the development of gastroprotection and endogenic NO. According to certain opinions (Konturek et al., 1994), NO which is biosynthetized from L-arginine (Moncada et al., 1991) has been implicated in the gastric protective effects of different antiulcer drugs e.g. aluminum-containing antacids. Besides, endogenous NO has shown to have a regulatory role in gastric mucosal blood flow (Lippe et al., 1992) and in mast cell reactivity (Salvemini et al. 1994), as well.

It is also evident from the above experiments that the degree of the gastroprotective action of zinc hyaluronates moreover exceeds—by one order—the effect of sucralfate, which is a representative anti-ulcer drug.

Non-steroidal anti-inflammatory drugs (NSAID) cause gastric lesions or in more severe cases gastric ulcers which is due to their direct damage to the gastric mucosa, topical irritation and to their indirect effect arising from the systemic inhibition of prostaglandin synthesis. Zinc hyaluronate (I), (II), (III) and (M) proved to be effective against indomethacin induced gastric damage, too. Comparing the effectiveness of zinc hyaluronate(II) with that of zinc hyaluronate (M), it can be concluded that the $ED_{50}$ values are nearly the same (5.8 mg/kg and 6.2 mg/kg, respectively), suggesting that—together with observations on the acidic ethanol-induced gastric lesion test—zinc hyaluronates regardless of the source they have been prepared from ("purum" or "puriss") have equal gastroprotective activities.

The results of indomethacin tests also support the view that zinc hyaluronate is more than just a simple physico-chemical barrier between the gastric lumen and gastric mucosa, since its action appears not only after oral (see: acidic alcohol test) but after subcutaneous administration, too.

It can be further concluded that zinc hyaluronates protect the gastric mucosa against the damaging effect of indomethacin. The protective action of zinc hyaluronates moreover exceed the effect of sucralfete as well.

The results of investigations on stress model provide further proof of the gastroprotective effect of zinc hyaluronate. These experiments are very important as one of the main causes of stress ulcer might be due to excess histamine release from the mast cells and it can not be excluded that the considerable gastroprotective effect of zinc hyaluronate against stress provoked lesions are likely to linked to its hypothesized mast cell stabilizing effect.

The results of PAF induced gastric damage further support the observation proved on acute models that zinc hyaluronate has an extraordinary gastroprotective action since zinc hyaluronate protected the gastric mucosa from the damaging effect on PAF. In addition, the results of investigations provide further evidences that zinc hyaluronate represents not only a physicochemical barrier over the gastric mucosa to protect it from damaging effect of locally acting chemicals but activates the protective mechanisms of gastric mucosa.

The highest importance of the results obtained on the acetic acid induced chronic ulcer model is to prove the observation that unlikely to e.g. $H_2$ blockers, zinc hyaluronate possesses activity not only in acute models, but also in a chronic ulcer model. Based on the results, it can be supposed that zinc hyaluronate stimulates the re-epithelization and so promotes the ulcer healing.

It can be seen from the results of the above model, too, that as for the effectiveness a significant difference exists between zinc hyaluronates having various molecular weights. Zinc hyaluronate with a molecular weight of 900.000 dalton proved to be more effective than zinc hyaluronate of higher or lower molecular weights, a fact demonstrating a relation between molecular weight and activity.

The results of experiments on the indomethacin induced intestinal ulcer model indicate that hyaluronate, beyond its outstanding gastroprotective effects, possesses intestinal protecting action as well, while sucralfate is totally ineffective in this test. The existence of such an effect further strengthens our view that zinc hyaluronate is more than a physicochemical barrier between the mucosa and intestinal lumen.

Beyond the investigation of effectiveness of zinc hyaluronates in different acute and chronic gastric models our aim was to examine whether or not it has any unwanted side-effect. Hence, the intestinal motility was investigated.

It is obvious from the experimental results that zinc hyaluronate does not change the intestinal motility. This property along with the increase in the $ED_{50}$ value of the acidified-ethanol induced gastric ulcer model after elevating the pretreatment time suggest that zinc hyaluronate does not stick to the gastric mucosa irreversibly and on the other hand it does not irritate the intestine to make it hyperactive.

Summarizing

Based on the results discussed and explained above, it can be proven that zinc hyaluronate can be considered to be a powerful gastroprotective agent, and its effectiveness surpasses that of sucralfate usually employed in the therapy of peptic ulcers.

It seems from the in vitro investigations that zinc hyaluronate inhibits the growth of Helicobacter pylori. It can be concluded that zinc hyaluronate may be useful in the cure of Helicobacter pylori-induced ulcers, too.

Due to its gastroprotective effect and simultaneous activity against Helicobacter pylori, zinc hyaluronate can be useful as supplementary therapy in the cure of Helicobacter pylori-induced ulcers or in a prophylactic treatment against re-infection. By its use, the amounts of antibiotics used in the therapy of Helicobacter pylori may possibly be reduced; as well as the anti-Helicobacter pylori agents used at present, which induce several side effects, may possibly be substituted.

Zinc hyaluronate can be converted to pharmaceutical compositions by mixing it with non-toxic, inert solid or liquid carriers and/or other auxiliaries which are commonly used in the therapy for enteral administration. Useful carriers are e.g.: water, gelatin, lactose, starch, pectin, magnesium-stearate, stearic acid, talc, vegetable oils such as peanut oil, olive oil and the like. The active ingredient may be formulated in any usual oral pharmaceutical composition, produced from a powder prepared in a known way, such as tablet, pellet, capsule, solution and the like. The active compound can preferably be administered in a form of concentrated aqueous solution, which may be prepared as described in Examples 1. and 4. The advantage of formulation as an aqueous solution is that no time is required for the active substance to dissolve in the gastric juice, the composition can be prepared without additives; and the daily dose can optionally and exactly be chosen.

The compositions can be prepared in a known manner by usual pharmaceutical technology and, if desired they may be subjected to other usual operations, e.g. sterilization.

The following Examples illustrate the compositions according to the invention and preparation thereof without limiting our claim to these Examples.

EXAMPLE 2

Tablets weighing 200 mg with 10 mg of active ingredient content

| | |
|---|---|
| Zinc hyaluronate | 10 mg |
| Lactose, anhydrous | 106 mg |
| Pregelated starch (Lycatos PGS) | 6 mg |
| Corn starch (Amylum maydis) | 40 mg |
| Microcrystalline cellulose (Avicel PH102) | 30 mg |
| Aerosil 200 | 1 mg |
| Talc | 6 mg |
| Magnesium stearate | 1 mg |

After the usual wet granulating of the active ingredient and additives, the mixture is compressed to tablets of 200 mg weight.

EXAMPLE 3

Pharmaceutical composition with 200 mg weight containing 10 mg of active ingredient formulated as pellets for use in sachet, vial or capsule.

| | |
|---|---|
| Zinc hyaluronate | 10 mg |
| Lactose | 95 mg |
| Microcrystalline cellulose (Avicel PH101) | 95 mg |

From the active ingredient and additives, a pellet is prepared in a known manner, e.g. in a vortex granulating equipment. The pellet is formulated in sachets, vials or capsules.

EXAMPLE 4

Pharmaceutical composition in the form of 100 ml of aqueous solution containing 1.0 g of active ingredient:

| | |
|---|---|
| Zinc hyaluronate | 1.0 g |
| Distilled water | q.s. 100 ml |

What is claimed is:

1. A method of treating a peptic ulcer or of preventing formation of a peptic ulcer in a patient which comprises the step of orally administering to said patient a therapeutically effective amount of a zinc hyalutonate complex having a molecular weight in the range of 500,000 to 1,200,000 daltons.

2. The method of treating a peptic ulcer defined in claim 1 wherein the zinc hyaluronate complex is administered together with a pharmaceutically acceptable inert carrier suitable for oral administration.

3. A method of preventing recurrence of a peptic ulcer in a patient having a healed peptic ulcer which comprises the step of orally administering to said patient a therapeutically effective amount of a zinc hyaluronate complex having a molecular weight in the range of 500,000 to 1,200,000 daltons.

4. The method of preventing recurrence of a peptic ulcer defined in claim 3 wherein the zinc hyaluronate complex is administered together with a pharmaceutically acceptable inert carrier suitable for oral administration.

* * * * *